(12) United States Patent
DePablo et al.

(10) Patent No.: US 6,919,172 B2
(45) Date of Patent: Jul. 19, 2005

(54) PRESERVATION AND STORAGE MEDIUM FOR BIOLOGICAL MATERIALS

(75) Inventors: Juan DePablo, Madison, WI (US);
Danforth Miller, Madison, WI (US);
Paul Conrad, Madison, WI (US);
Horacio Corti, Lanus Buenos Aires (AR)

(73) Assignee: Wisconsin Alumni Research Foundation, Madison, MI (US)

( * ) Notice: Subject to any disclaimer, the term of this patent is extended or adjusted under 35 U.S.C. 154(b) by 0 days.

(21) Appl. No.: 10/657,017

(22) Filed: Sep. 5, 2003

(65) Prior Publication Data

US 2004/0043374 A1 Mar. 4, 2004

Related U.S. Application Data

(62) Division of application No. 09/625,735, filed on Jul. 26, 2000, now Pat. No. 6,653,062.

(51) Int. Cl.$^7$ .............................. A01N 1/00; A01N 1/02; A61K 31/7012
(52) U.S. Cl. ................................. 435/1.1; 435/2; 514/53
(58) Field of Search ............................. 435/1.1, 2, 6, 7, 435/188, 1.3; 514/53, 59, 832; 424/199, 93.7; 536/112

(56) References Cited

U.S. PATENT DOCUMENTS

| | | | |
|---|---|---|---|
| 4,411,894 A | 10/1983 | Schrank et al. | |
| 4,476,221 A | 10/1984 | Kane et al. | |
| 4,798,824 A | 1/1989 | Belzer et al. | |
| 4,806,343 A | 2/1989 | Carpenter et al. | |
| 4,806,524 A | 2/1989 | Kawaguchi et al. | |
| 4,857,319 A | 8/1989 | Crowe et al. | |
| 4,873,230 A | 10/1989 | Belzer et al. | |
| 4,891,319 A | 1/1990 | Roser | |
| 5,026,566 A | 6/1991 | Roser | |
| 5,149,653 A | 9/1992 | Roser | |
| 5,171,661 A | 12/1992 | Goodrich, Jr. et al. | |
| 5,252,496 A | 10/1993 | Kang et al. | |
| 5,314,595 A | 5/1994 | Fuller | |
| 5,512,547 A | 4/1996 | Johnson et al. | |
| 5,556,771 A | 9/1996 | Shen et al. | |
| 5,589,167 A | 12/1996 | Cleland et al. | |
| 5,621,094 A | 4/1997 | Roser et al. | |
| 5,827,741 A | 10/1998 | Beattie et al. | |
| 6,468,782 B1 | 10/2002 | Tunnacliffe et al. | |
| 2001/0019819 A1 | 9/2001 | Wolkers et al. | |
| 2002/0009500 A1 | 1/2002 | Wolkers et al. | |
| 2002/0076445 A1 | 6/2002 | Crowe et al. | |
| 2002/0114791 A1 | 8/2002 | Crowe et al. | |

FOREIGN PATENT DOCUMENTS

| | | |
|---|---|---|
| EP | 0 356 257 | 2/1990 |
| EP | 0 508 496 | 10/1992 |
| EP | 0 580 444 | 1/1994 |
| EP | 0 682 944 | 11/1995 |
| WO | WO 95/20399 | 8/1995 |
| WO | WO96/05809 | 2/1996 |
| WO | WO96/40077 | 12/1996 |
| WO | WO98/41188 | 9/1998 |
| WO | WO99/47174 | 9/1999 |

OTHER PUBLICATIONS

Ahmad N, Kashi H, Helmy H, Hadingham J, Potts DJ, Lodge JP. Renal preservation with phosphate buffered sucrose: comparison with hyperosmolar citrate in a prospective trial. Transplant Proc. Feb.–Mar. 1997;29(1–2):355–6.
Arakawa et al., Stabilization of Protein Structure By Sugars, Biochemistry 21, 6536–6544, 1982.
Bando et al., Effects of Newly Developed Solutions Containing Trehalose on Twenty–Hour Canine Lung Preservation, The Journal of Thoracic and Cardiovascular Surgery 108, 1:92–98, 1994.
Beattie et al., Trehalose: A Cryoprotectant that Enhances Recovery and Preserves Function of Human Pancreatic Islets After Long–Term Storage, Diabetes 46, 519–523, 1997.
Carpenter et al., Interactions of Stabilizers with Proteins During Freezing and Drying, American Cancer Society 9, 135–147, 1994.
Carpenter et al., Long–Term Preservation of Dried Phosphofructokinase by Sugars and Sugar/Zinc Mixtures, Cryobiology 25, 372–376, 1998.
Carpenter et al., Modes of Stabilization of a Protein by Organic Solutes During Desiccation, Cryobiology 25, 459–470, 1998.
Carpenter et al., Stabilization of Phosphofructokinase During Air–Drying with Sugars and Sugar/Transition Metal Mixtures, Cryobiology 24, 455–465, 1987.

(Continued)

Primary Examiner—Jon Weber
Assistant Examiner—Sheridan Snedden
(74) Attorney, Agent, or Firm—Joseph T. Leone, Esq.; DeWitt Ross & Stevens S.C.

(57) ABSTRACT

A protectant mixture for use in preserving biological materials comprising (1) at least one polyhydroxy compound, where the total amount of polyhydroxy compound in the mixture is from about 5% to about 60% by weight of the mixture where the mixture is an aqueous solution and is from about 10% to about 95% where the mixture is in solid form, and (2) phosphate ions, where the total amount of phosphate ions in the mixture is such that the molar ratio of phosphate ions to hydroxy groups in the polyhydroxy compound is from about 0.025 to about 0.625; a preservation medium comprising (1) a biological material, (2) at least one polyhydroxy compound, where the total amount of polyhydroxy compound in the medium is from about 5% to about 60% by weight of the medium, and (3) phosphate ions, where the total amount of phosphate ions in the mixture is such that the molar ratio of phosphate ions to hydroxy groups in the polyhydroxy compound is from about 0.025 to about 0.625; methods of preserving the preservation medium; and the resulting preserved biological material composition.

15 Claims, 5 Drawing Sheets

OTHER PUBLICATIONS

Carpenter et al., Stabilization of Phosphofructokinase with Sugars During Freeze–Drying: Characterization of Enhanced Protection in the Presence of Divalent Cations, *Biochimica et Biophysica Acta*, 109–115, 1987.

Carpenter et al., The Mechanism of Cryoprotection of Proteins by Solutes, *Cryobiology* 25, 244–255, 1998.

Crowe et al., Is Trehalose Special for Preserving Dry Biomaterials?, *Biophysical Journal*, Chpt. 71, 2087–2093, 1996.

Crowe et al., Preservation of Freeze–Dried Liposomes by Trehalose, *Archives of Biochemistry and Biophysics* 242, 240–267, 1985.

Crowe et al., Preservation of Mammalian Cells–Learning Nature's Tricks, *Nature Biotechnology* 18, 145–167, 2000.

Crowe et al., Preserving Dry Biomaterials: The Water Replacement Hypothesis, Part 1, *BioPharm* 37, 28–33, 1993.

Crowe, et al., *Cryobiology*, 20, 346–356, 1983.

Crowe, et al., *Cryobiology*, 35, 20–30, 1997.

Crystall, Glass Pharmacy: Preserved in Minute Beads of Sugar, Drugs Could Last for Years and Be Easier to Take, Too., *New Scientist*, 24–27, 1997.

Darling, et al., *Animal Cells–Culture and Media–Essential Data* 22–23, John Wiley & Sons 1994.

Dellman et al., Preservation of Fine Structure in Vibratome–Cut Sections of the Central Nervous System Stained for Light Microscopy, *Stain Technology* 58, 6:319–23, 1983.

Dulbecco, et al., "Plaque Formation and Isolation of Pure Lines with Poliomyelitis Viruses" *Journal of Experimental Medicine*, 99:167–182, 1954.

English Translation of Fukumoto et al.

English Translation of Migulina.

Eroglu et al., Intracellular Trehalose Improves the Survival of Cryopreserved Mammalian Cells, *Nature Biotechnology* 18, 163–167, 2000.

Ford et al., The Effect of Carbohydrate Additives in the Freeze–Drying of Alkaline Phosphate, *J. Pharm Pharmacol* 45, 86–93, 1992.

Franks et al., Using Water Soluable Glasses as a Strategy for Bioproduct Stabilization, *Pafra Biopreservation*, Cambridge, U.K., 1 pg.

Freshney, *Culture of Animal Cells*, $3^{rd}$ Ed., 85, Wiley–Liss, 1994.

Freshney, *Culture of Immortalized Cells* 186, Wiley–Liss, 1996.

Fukumoto et al., Effect of Various Additives on Long–Term Preservation of Cucumber Mosaic in vitro, *Ann. Phytophath Soc.* Japan 46, 448–54, 1980.

Goldin, Barry R., "Health Benefits of Probiotics" *British Journal of Nutrition* 80 Suppl. 2, S203–S207, 1998.

Guo et al., Trehalose Expression Confers Desiccation Tolerance on Human Cells, *Nature Biotechnology* 18, 168–171, 2000.

Hirata et al., Effects of Trehalose in Canine Lung Preservation, *Surgery* 115, 1:102–107, 1994.

Hopkinson et al., Comparison of Saccharides as Osmotic Impermeants During Hypothermic Lung Graft Preservation, *Transplantation* 61, 12:1667–1671, 1996.

Isowa et al., Trehalose–Containing Solutions Enhance Preservation of Culture Endothelial Cells, Ann. Thoracic Surgery, 61:542–545, 1996.

Izutzu et al., Cryprotection of LDH of Amphiphilic Excipients, *Biotechnology and Bioengineering* 43, No. 11, 1994.

Izutzu et al., Stabilizing Effect of Amphiphilic Excipients on Freeze–Thawing and Freeze–Drying of Lactate Dehydrogenase, *Biotechnology and Bioengineering* 43, 1102–1107, 1994.

Kaufman, et al., Ed., *Handbook of Molecular and Cellular Methods in Biology and Medicine* 350, CRC Press, 1995.

Kharche et al., Effect of Certain Dilutors on the Morphology of Ram Spermatoza on Preservation at 5C, *Indian Vet.* S 53, 694–98, 1976.

Kitahara, et al., Preservation of Skin Free–Flap Using Trehalose, *Journal of Surgical Research* 62, 1:130–134, 1996.

Lam FT, Mavor Al, Potts DJ, Giles GR. Improved 72–hour renal preservation with phosphate–buffered sucrose. *Transplantation*. May 1989;47(5):767–71.

Leslie et al., Trehalose and Sucrose Protect Both Membranes and Proteins in Intact Bacteria During Drying, *Applied Environmental Microbiology* 61, 3562–3597, 1995.

McCoy II, Cryobio Research May Lead to Increased Human Blood Supply, Mary Ann Liebert, Inc., New York, 1994.

Migulina, Preservation of Sheep's Blood for the Wasserman Reaction with Glucoboric–Saline Solution, *Vestn. Derm. Vener* 35, 3:40–47, 1961.

Miller et al., Monitor: Progress and Profiles, *PSST* 1, No. 7, 1998.

Miller et al., Stabilization of Lactate Dehydrogenase Following Freeze–Thawing and Vacuum–Drying in the Presence of Trehalose and Borate, *Pharmaceutical Research* 15, 8:1215–1221, 1998.

Miller, et al., "Thermoph;ysical Properties of Trehalose and Its Concentrated Aqueous Solutions" *Pharmaceutical Research* 14, 5:578–590, 1997.

Onishi and Barr, "Simplified Method for Quantitating Protein using Biuret and Phenol Reagents" *Analytical Biochem* 86:193–200, 1978.

Perzon et al., Reversible Gel Formation Induced by Ion Complexation, *Macromolecules* 21, 1121–1125, 1998.

Pollard, et al., Ed., *Basic Cell Culture Protocols* $2^{nd}$ Ed., 471, Humana Press, 1997.

Roser et al., A Sweeter Way to Fresher Food, *New Scientist*, 1993, 4 pgs.

Saha et al., Normal Calves Obtained After Direct Transfer of Vitrified Bovine Embryos Using Ethylene Glycol, Trehalose and Polyvinylpyrrolidone, *Cryobiology* 33, 291–299, 1996.

Sanders, Mary E., "Development of Consumer Probiotics for the US Market" *British Journal of Nutrition* 80, Suppl. 2, S213–S218, 1998.

Sigma Product Information: Product No. P0261.

Spieles, et al., *Cryo–Letters* 17, 43–52, 1996.

Sutton, J., *Chem. Soc. Faraday Trans* 87, 3747, 1991.

Vaughan et al., Probiotics in the New Millenium, *Nahrung, (Food)* 43, 3:148–153, 1999.

Whitaker, *Tissue and Cell Culture* 14–15, Balliere Trindall, 1972.

Yokomise et al., Long–Term Cryopreservation Can Prevent Rejection of Canine Tracheal Allografts with Preservation of Graft Viability, *The Journal of Thoracic and Cardiovascular Surgery* 111, 5:930–934, 1996.

Zuidam et al., Gamma–Irradiation of Non–Frozen, Frozen, and Freeze–Dried Liposomes, *Pharmaceutical Research*, 12(11):1761–68, 1995.

PRESERVATION AND STORAGE MEDIUM FOR BIOLOGICAL MATERIALS

CROSS-REFERENCE TO RELATED APPLICATIONS

This application is a divisional of U.S. application Ser. No. 09/625,735, filed Jul. 26, 2000.

STATEMENT REGARDING FEDERALLY SPONSORED RESEARCH OR DEVELOPMENT

This invention was made with United States government support awarded by the following Agencies:

NSF 9901430

The United States has certain rights in this invention.

FIELD AND BACKGROUND OF THE INVENTION

The present invention relates generally to preserving and stabilizing biological materials by freezing, drying, and freeze-drying, and more specifically to protectant mixtures and aqueous preservation media for preserving biological materials, as well as methods of preserving biological materials and the preserved biological material compositions themselves.

The preservation of the structure and function of biological molecules is of fundamental importance to biology, biochemistry, and medicine. Biological materials, such as proteins, enzymes, cells, tissues, nucleic acid, semen, blood and its components, mammalian organs, and foodstuffs must often be stored and preserved for later use. Preservation of these biological materials is usually achieved by either freezing or drying, or a combination of the two processes. There are several commonly-used drying techniques: drying by evaporation into a moving gas stream (ambient air-drying), drying under vacuum at ambient temperatures (vacuum-drying), or drying by contacting a fine mist of droplets with warm air (spray-drying). Simple freezing is often done when drying is either harmful or unnecessary. Certain biological materials are best preserved by freeze-drying (lyophilization), a two-step process in which the sample is first frozen and then dried at low temperature under vacuum.

The structure and function of most biological materials is dependent upon their aqueous environment. Therefore, changes to their aqueous environment resulting from freezing and drying processes can often have drastic consequences for a biological material. Furthermore, freeze-drying combines the stresses due to both freezing and drying. The freezing step of this process can have undesirable side effects, such as the denaturation of proteins and enzymes, and rupture of cells. These effects result from mechanical, chemical, and osmotic stresses induced by crystallization of ice in these materials. As a result, the activity of the biological material upon rehydration is lost either in its entirety, or to such a significant extent that the material is no longer useful for its intended purpose.

To prevent or reduce the adverse effects upon reconstitution or rehydration, protective agents, such as cryoprotectants or lyoprotectants (freeze-drying) are used. For such protective agents to be effective, they must be non-toxic to the biological material at the concentrations encountered during the preservation process, and must interact favorably with water and with the biological material. Various protective agents have been used in the art, with varying degrees of success. These include fish proteins, certain polymers, skim milk, glycerol, dimethyl sulfoxide, and disaccharides, such as trehalose. Unfortunately, suitable protective agents and cryopreservation protocols have been developed only for a limited number of systems.

Disaccharides, such as sucrose and trehalose, are natural cryoprotectants. Trehalose is a particularly attractive cryoprotectant because it has actually been isolated from plants and animals that remain in a state of suspended animation during periods of drought. Trehalose has been shown to be an effective protectant for a variety of biological materials, both in ambient air-drying and freeze-drying. Research has shown, (see Crowe, J. H., Crowe., L. M., and Mouriadian, R., *Cryobiology*, 20, 346–356 (1983)), that liposomes dried in the presence of trehalose retain both their functional and structural integrity upon rehydration. U.S. Pat. No. 5,556,771 discloses the use of trehalose, or trehalose in combination with polyvinylpyrrolidone to preserve reverse transcriptase and RNA polymerase. U.S. Pat. No. 5,512,547 discloses the use of trehalose to preserve botulinum neurotoxin. Likewise, U.S. Pat. No. 4,891,319 discloses a method of protecting proteins and other biological macromolecules, such as enzymes, serum, serum complement, antibodies, antigens, fluorescent proteins and vaccine components using trehalose. Specifically, an aqueous mixture containing the macromolecule and trehalose is dried at a temperature above freezing in the presence of 0.05 to about 20% trehalose by weight of the aqueous system.

However, there are some drawbacks associated with the use of trehalose as the sole cryoprotectant. To preserve many biological materials by freeze-drying, large amounts of trehalose must be used; concentrations of trehalose greater than 60% by weight of a given preservation medium are sometimes necessary. This is costly. Further, a high concentration of trehalose reduces the solubility of other solutes in the system.

Thus, it has been proposed to use trehalose in combination with a polymeric gelling agent, such as carboxymethylcellulose or carboxyethylcellulose. It has been suggested for human blood that saccharides combined with polymers are even more effective cryoprotectants than pure trehalose. See U.S. Pat. No. 5,171,661; Sutton, R. L., *J. Chem. Soc. Faraday Trans.*, 87, 3747 (1991). Unfortunately, attempts to confirm the beneficial effect of the gelling agents have been unsuccessful. (G. Spieles, I. Heschel, and G. Rau, *Cryo-Letters* 17, 43–52 (1996), J. H. Crowe, A. E. Oliver, F. A. Hoekstra, and L. M. Crowe, *Cryobiology* 35, 20–30 (1997) .). Moreover, this protective combination cannot be used for medical purposes, because the polymer gelling agents are not accepted well by the human body. As a result, this combination is not very useful, and does not provide much, if any, practical improvement over the use of trehalose alone.

Another, more serious problem associated with the use of trehalose is that biological materials preserved using trehalose alone are not storage stable for extended periods of time, especially those stored at superambient temperatures and/or in humid environments. In other words, biological materials preserved with trehalose can lose their activity in a matter of hours or days, depending on the humidity and temperature of the storage conditions.

Therefore, at present, freeze-drying with trehalose is of limited use for extended term storage of biological materials, such as proteins, enzymes, cells, tissues, nucleic acid, semen, blood and its components, mammalian organs, and foodstuffs, over a wide range of storage conditions, because the material will degrade, and will not have sufficient activity upon reconstitution. From a practical standpoint, this is clearly unacceptable for medical products, as one of the reasons for preserving the materials in the first place is to provide a storage-stable product.

Nor can many of the various room temperature drying techniques be effectively used at present. These methods, while less complicated and less costly than freeze-drying, are generally more destructive to biological materials. Many biological materials are more prone to gross conformational changes and unwanted reactions when preserved using methods that take place at ambient temperature than when freeze-drying is used. As a result, even where presently known protective agents are used, the activity of many rehydrated biological materials is both unsatisfactory in its own right, and significantly less than if preserved by freeze-drying.

Thus, a need exists for a protectant mixture that is useful for a wide range biological materials. A further need exists for a protectant mixture that can be effectively used in both freeze-drying processes and drying processes involving ambient-temperature drying. There is also a need for a protectant mixture that is less costly than those presently being used. Finally, and very importantly, there is a need for a protectant mixture that provides stable media for preservation of biological materials over extended periods of time at elevated temperatures and varying degrees of humidity, which can be encountered during shipping and storage of materials, while still retaining a significant amount of activity upon rehydration.

All of these needs are met by the protectant mixture, aqueous protective medium and resulting preserved biological material compositions of the present invention.

SUMMARY OF THE INVENTION

It has been found that a protectant mixture for use in preserving biological materials, comprising: (a) at least one polyhydroxy compound, where the total amount of polyhydroxy compound in the mixture is from about 5% to about 60% by weight of the mixture if the mixture is an aqueous solution and from about 10% to about 95% by weight if the mixture is in solid form; and (b) phosphate ions, where the total amount of phosphate ions in the medium is such that the molar ratio of phosphate ions to hydroxyl groups in the polyhydroxy compound is from about 0.025 to about 0.625, can be used with a wide variety of biological materials to provide an aqueous preservation medium. This aqueous preservation medium can then be used in a multiplicity of preservation processes, including freezing, freeze-drying and other drying processes, such as spray-drying, vacuum-drying, or ambient air-drying, to provide a stable, preserved composition of the biological material of interest. This preserved composition is stable for extended periods of time at superambient temperatures and/or relative humidity. Further, when the preserved biological material composition is rehydrated, the structural and functional integrity of the preserved biological material has been retained to such an extent that the biological material can be used for its intended purpose.

Therefore, the present invention also provides a method for preparing a preserved biological material composition from the above-noted preservation medium, as well as the preserved biological material composition itself.

DESCRIPTION OF THE PREFERRED EMBODIMENTS

The present invention is based on the remarkable discovery that biological materials can be preserved while retaining substantial activity, when the biological material is combined with the protectant mixture of the present invention to form an aqueous preservation medium, which in turn is formed into a preserved biological material composition by subjecting the aqueous preservation medium of the present invention to (1) various drying techniques, including freeze-drying, ambient air-drying, vacuum-drying, and spray-drying, or (2) other preservation methods known in the art, such as freezing. The protectant mixture of the present invention comprises: (a) at least one polyhydroxy compound, where the total amount of polyhydroxy compound in the mixture is from about 5% to about 60% by weight of the mixture if the mixture is an aqueous solution and from about 10% to about 95% by weight if the mixture is in solid form; and (b) phosphate ions, where the total amount of phosphate ions in the mixture is such that the molar ratio of phosphate ions to hydroxyl groups in the polyhydroxy compound is from about 0.025 to about 0.625. The aqueous preservation medium of the present invention comprises: (a) a biological material; (b) at least one polyhydroxy compound, where the total amount of polyhydroxy compound in the medium is from about 5% to about 60% by weight of the medium; and (c) phosphate ions, where the total amount of phosphate ions in the medium is such that the molar ratio of phosphate ions to hydroxyl groups in the polyhydroxy compound is from about 0.025 to about 0.625.

Biological Materials

A wide range of biological materials can be used with the inventive protectant mixtures to form the aqueous preservation medium of the present invention. This preservation medium can then be subjected to the processes of the present invention to make a preserved biological material composition. These biological materials, include, without limitation:

(a) enzymes, such as lactate dehydrogenase and phosphofructokinase;
(b) proteins, such as insulin;
(c) serum complement;
(d) vaccines;
(e) tissue, including skin, veins and arteries;
(f) viruses, such as adenovirus;
(g) mammalian organs, such as the liver, pancreas and lungs;

(h) blood, and its components, including red blood cells, white blood cells and platelets;

(i) cells, including prokaryotic cells (including bacteria) and eukaroytic cells;

(j) semen;

(k) other biological materials, including nucleic acids, and lipid vesicles; and (l) foodstuffs.

The above is merely exemplary of some of the myriad of biological materials that can be made into the preserved biological material compositions of the claimed invention using the protectant mixture, aqueous preservation medium and process of the claimed invention. Any biological material for which preservation for later use is desirable can be used with the protectant mixture, to form the preservation media, which can then be preserved by the preservation methods of the invention to form preserved compositions.

Polyhydroxy Compound

Polyhydroxy compounds useful in the present invention include natural and synthetic monosaccharides and polysaccharides, other carbohydrates, and polyalcohols and their derivatives. Here, "polysaccharides" are defined as saccharides containing two or more monosaccharide units. The individual polyhydroxy compounds can be used singly, or in combination with other types of polyhydroxy compounds. From the wide variety of useful polyhydroxy compounds, the use of monosaccharides and polysaccharides is preferred. Of the saccharides, disaccharides, such as trehalose, maltose, lactose, and sucrose are preferred for use in the present invention, with trehalose being most preferred.

The amount of polyhydroxy compound present in the protectant mixture, preservation medium, and preserved composition of the present invention depends upon the specific polyhydroxy compounds, and biological material selected for use, as well as the mass of biological material being preserved. This can be adjusted and optimized for a given system.

Generally, the polyhydroxy compounds are present in the protectant mixture of the present invention in a total amount of from about 5% to about 60% by weight of the mixture, where the mixture is an aqueous solution. Where the protectant mixture is supplied as a solid, for example as a powder, the polyhydroxy compounds should be present in a total amount of from about 10% to about 95% by weight of the mixture, with an amount in the range of about 20% to about 95% by weight of the mixture being preferred. Where the protectant mixture is an aqueous solution, the polyhydroxy compounds are preferably present in a total amount such that the total amount of polyhydroxy compound in the mixture is from about 5% to about 40% by weight of the mixture, with an amount in the range of about 10% to about 30% by weight of the mixture being particularly preferred.

Likewise, the polyhydroxy compounds should be present in the preservation medium of the present invention in an amount such that the total amount of polyhydroxy compounds in the aqueous preservation medium is from about 5% to about 60% by weight of the aqueous preservation medium. Preferably, the total amount of polyhydroxy compound present should be from about 5% to about 40% by weight of the aqueous preservation medium, with an amount in the range of about 10% to about 30% by weight of the aqueous preservation medium being particularly preferred.

It should be emphasized that the above ranges can be varied, for example, depending upon the amount of biological material in the preservation medium and the preservation method chosen for use.

Use of the above amounts of polyhydroxy compound in the aqueous preservation medium of the present invention will upon partial or complete removal of liquid water, result in a preserved biological material composition having from about 5% to about 95% polyhydroxy compound by weight of the composition. Again, this amount will depend on the mass of the biological material being preserved, the amount of phosphate present, and the amount of water removed from the system during preservation. The amount of polyhydroxy compound in the preserved biological composition can be determined from the amount present in the protectant mixture and/or aqueous preservation medium. Alternatively, the amount of polyhydroxy compound in the preserved biological material composition can be determined by analytical methods known in the art, such as column chromatography.

Phosphate Ions

Any source of phosphate ions can be used in the protectant mixture, preservation medium, preservation process, and preserved composition of the present invention. While not wishing to be bound by any particular theory, it is believed that the phosphate ions form a complex with the polyhydroxy compound, which may contain several molecules of the polyhydroxy compound in a three-dimensional supermolecular structure cross-linked by the phosphate ions. The aqueous preservation medium has a much higher viscosity than a system containing the polyhydroxy compound alone in the same amount, and the preserved biological material composition has a higher glass transition temperature ($T_g$) than a composition containing only the polyhydroxy compound.

As stated earlier, the phosphate ions can be provided from any source, including acids and salts. The use of sodium and potassium salts are preferred. Potassium salts are most preferred, because they have excellent solubility characteristics at low temperature, and crystallize as anhydrous crystals. Therefore, the phosphate ions are preferably provided through the use of sodium and/or potassium salts, with the use of a mixture of monobasic and dibasic potassium phosphate being particularly preferred.

The amount of phosphate ion that is optimal for a given protectant mixture and/or preservation medium depends on several variables, including the specific biological material to be preserved, the amount and type of polyhydroxy compound in the protectant mixture and/or preservation medium, and the amount of biological material in the system. Generally, phosphate ions should be present in the protectant mixture and/or aqueous preservation medium in a total amount such that the molar ratio of phosphate ions to hydroxyl groups in the polyhydroxy compound is from about 0.025 to about 0.625. Preferably, the phosphate ions are present in an amount such that the molar ratio of phosphate ions to hydroxyl groups in the polyhydroxy compound is from about 0.0375 to about 0.625.

The molar ratio of phosphate ions to hydroxyl groups in the polyhydroxy compound will remain substantially constant throughout the preservation process, resulting in a preserved biological material having substantially the same molar ratio of phosphate ions to hydroxyl groups in the polyhydroxy compound. Thus, the amount of phosphate ions present in the preserved biological material composition follows directly from the amount present in the aqueous preservation medium. Alternatively, the amount of phosphate ions in the preserved biological material composition can be determined analytically by methods known in the art, including ion chromatography and chemiluminescence.

The useful amount of phosphate ions can also be determined on the basis of moles of phosphate ion per moles of the polyhydroxy compound by multiplying the above ratios by the number of hydroxyl groups present per mole of the polyhydroxy compound being used. For example, trehalose and sucrose have 8 moles of hydroxyl groups per mole of compound. Therefore, where trehalose or sucrose is used as the polyhydroxy compound, the ratio of from about 0.025 to about 0.625 moles of phosphate ions per mole of hydroxyl groups can be achieved by adding sufficient phosphate ions to achieve a molar ratio of phosphate ions to sucrose or trehalose of about 0.2 to about 5. For trehalose or sucrose, the preferred molar ratio of from about 0.0375 to about 0.625 translates to a molar ratio of phosphate ions to sucrose or trehalose of from about 0.3 to about 5.

It has been found that the effectiveness of the phosphate ions in stabilizing and preserving the structure and function of a given biological material increases as the molar ratio of phosphate ions to hydroxyl groups increases from zero, but only up to a point (the optimum ratio), after which the use of additional phosphate ion provides no or only a slight increase in effectiveness. As discussed previously, the optimal ratio depends on several factors, including the amount and type of biological material used, the amount and type of polyhydroxy compounds in the preservation medium, the pH of the preservation medium, and the preservation technique to be utilized.

The use of phosphate ions at a molar ratio of phosphate ions to hydroxyl groups in the polyhydroxy compound that is higher than that found to be optimal for a given aqueous preservation medium of the present invention may, in many circumstances, still result, upon preservation, in a preserved biological material composition having improved structural and functional integrity, such as improved activity on rehydration, storage stability, or advantages in cost or processing over a preserved composition resulting from an aqueous preservation medium containing only the polyhydroxy compound. Therefore, it is preferred that the ratio for a given aqueous preservation medium of the present invention be less than or equal to that resulting in optimal stability and activity upon rehydration, with the use of the optimum ratio being most preferred. However, an aqueous preservation medium having a ratio greater than that needed for optimal activity of the preserved biological material upon rehydration can be used.

Other Components

The protectant mixture and/or aqueous preservation medium of the present invention can contain other components. For example, they may contain a buffer to maintain the pH of the medium at an optimal value for a given biological material. It should be noted that the phosphate ions in the mixture and/or medium function as a buffer as well, so additional non-phosphate buffers may not be needed. If a phosphate buffer is used, the amount of phosphate ions present in the buffer should be included in determining the molar ratio of phosphate ions to hydroxyl groups of the polyhydroxy compound in the mixture and/or aqueous preservation medium, as well as the resulting preserved biological material composition. The pH at which a given biological material is most stable is known in the art. Generally, the preservation media of the present invention should have a pH in the range from about 5 to about 10, with a pH in the range from about 6 to about 9 being most preferred.

The protectant mixture and/or aqueous preservation medium may also contain one or more antioxidants, such as sodium thiosulfate, ascorbic acid, citric acid, and sodium citrate. If an antioxidant is used, it can be present in an amount known to be useful in the art.

The protectant mixture and/or aqueous preservation medium may also contain other components that may act as drying agents and/or osmoprotectants, such as methanol, ethanol, glycerol and DMSO. These components tend to reduce residual moisture or balance osmotic stresses in the preserved biological material compositions made from the aqueous preservation media of the present invention, which may in some cases result in better storage capability.

Preparation of the Protectant Mixture, Aqueous Preservation Medium and Preserved Composition of the Present Invention The protectant mixture of the present invention can be prepared as follows. The polyhydroxy compound and the source of phosphate ions are added in the desired proportion to an aqueous solution. It is preferred that the phosphate ion source be dissolved in the solution prior to the addition of the polyhydroxy compound. The mixture may be heated if necessary to effect dissolution. The solution should be mixed thoroughly, until a homogenous protectant mixture is obtained. This protectant mixture can then be stored as an aqueous solution, or can be subjected to various processes known in the art to produce a solid mixture, such as a powder. The powder can be anhydrous or a partially crystalline hydrated material. Where the protectant mixture is a solid, such as a powder, it should be reconstituted with an aqueous solution before it is used to make the aqueous preservation medium of the present invention. However, the solid mixture can be directly added to an aqueous solution containing the biological material to form the aqueous present medium.

The protectant mixture in the form of an aqueous solution is then added to an aqueous solution of the biological material. If the protectant mixture was prepared in an aqueous buffer solution, the aqueous solution of biological materials is preferably prepared in the same buffer. These two solutions are then thoroughly mixed, to form the aqueous preservation medium of the present invention. If an antioxidant is being used, it is generally added to the aqueous solution of biological material before addition of the protectant solution.

The amount of biological material used in the aqueous preservation medium of the present invention can be varied as desired, depending for example upon the specific biological material to be preserved, the amounts of phosphate ions and polyhydroxy compound present, the preservation technique to be employed.

The aqueous preservation medium can then be preserved by one or more techniques known in the art, including freezing, freeze-drying, vacuum-drying, ambient, air-drying, and/or spray-drying, to provide a preserved biological material composition of the present invention. The resulting preserved biological material composition can be anhydrous, or can be a partially crystalline hydrated material. It is preferred that the preserved biological material be substantially anhydrous in nature. Here, "substantially anhydrous" means that the preserved biological material composition contains less than 10% water measured by Karl Fisher analysis.

EXAMPLE 1

Various protectant mixtures in aqueous solution form were made in Butterfield's buffer (0.6 mM potassium phosphate buffered water having a pH of 7.2), by adding predetermined amounts of a polyhydroxy compound and phosphate ions, and mixing to form a homogenous solution. A given protectant mixture was then added to an *L. acidophilus* cell solution in a 1:1 mass ratio, and the resulting aqueous protective medium was thoroughly mixed and allowed to incubate at room temperature for 30 minutes. The *L. acido-*

*philus* cell solution was prepared as follows: concentrated *L. acidophilus* bacterial cultures having a 15.3 wt % dry mass were mixed with 1.9% sodium thiosulfate to form an *L. acidophilus* cell solution and allowed to incubate at room temperature for 30 minutes.

Samples of each aqueous protective medium made in the above manner were then subjected to either freezing, freeze-drying or vacuum-drying.

For the samples that were frozen, the aqueous preservation medium was dripped through a 25 gauge syringe needle into liquid nitrogen. The drops usually formed pellets of 2–3 mm in diameter, which froze completely within about 10 seconds. These samples of preserved cell composition were then allowed to thaw in open atmosphere at room temperature.

The samples that were freeze-dried were subjected to freezing as detailed above, and the resulting pellets were placed in a Virtis 12EL freeze dryer on precooled shelves at a temperature no greater than −45° C. Additionally, small samples of the preservation medium were weighed to determine their density, and then freeze-dried as a thin layer in glass dishes. These samples were weighed before and after freeze-drying to calculate the amount of water lost by each sample during freeze-drying, and hence to determine the amount of water needed for rehydration.

All of the freeze-dried samples were subjected to the following freeze-drying protocol, where the pressures and temperatures are set points. After the samples were placed in the freeze dryer as discussed above, the freeze dryer was evacuated with a pressure of 0 mtorr. The samples were held at −45° C. and 0 mtorr for 1200 minutes, after which the temperature and pressure were increased to −40° C. and 20 mtorr, respectively, over a period of 50 minutes. The samples where then held at −40° C. and 20 mtorr for 600 minutes. The temperature was then increased to −35° C. over a period of 50 minutes, and the samples were then held at −35° C. and 20 mtorr for 600 minutes. The temperature and pressure were next increased to −30° C. and 50 mtorr, respectively, over 50 minutes and the samples were then held at −30° C. and 50 mtorr for 600 minutes. At the end of that period of time, the temperature and pressure were increased to −25° C. and 100 mtorr, respectively, over 50 minutes, and the samples were held at −25° C. and 100 mtorr for 600 minutes. The temperature was then increased to −20° C. over 50 minutes, and the samples were then held at −20° C. and 100 mtorr for 600 minutes. The temperature was next increased to −10° C. over 100 minutes, and the samples were held at that temperature and 100 mtorr for 600 minutes.

The samples were then increased to a final temperature of 40° C. at a rate of 0.5° C./min, at 50 mtorr. The samples were then held at the final temperature at 0 mtorr for 1200–2400 minutes. The freeze dryer was then vented with nitrogen gas, and the preserved cell composition samples were removed, sealed in 50 ml plastic centrifuge tubes, and stored in a 37° C. incubator.

For the samples that were subjected to vacuum drying, 0.2 ml of the preservation medium was placed in a 1.8 ml plastic microcentrifuge tube. The samples were then placed into a Savant Instruments SVC-100H SpeedVac Concentrator vacuum dryer and rotary evaporated at room temperature for approximately 4 days at a final pressure of 85 mtorr, to obtain preserved cell compositions. The tubes were then sealed, and stored at room temperature in a desiccator.

At the time the samples were made and subjected to freezing, vacuum-drying or freeze-drying, additional samples from the aqueous preservation media were taken, diluted, and plated on agar medium using a standard pour-plating technique to determine the viable cell number in the preservation medium prior to any preservation process being conducted. First, the samples were diluted to achieve a cell concentration of about 100 cells/ml. One or two milliliters of the diluted preservation medium were then placed in a petri dish and mixed with liquid agar growth medium (15 g/L agar with 55 g/L MRS Lactobacillus Broth and 0.1% L-cysteine) at 45° C. The dish was allowed to cool, solidifying the agar, at which time the dishes were inverted and placed in an anaerobic growth chamber (GasPak jar) at 37° C. for 2–3 days, at which time colonies were visible in the agar. In principle, each colony represents a single viable cell in the preservation medium.

At various times, portions of the preserved cell compositions prepared by freeze-drying and vacuum drying were rehydrated in Butterfield's buffer. Freeze-dried samples were rehydrated to approximately $1/100^{th}$ of their original concentration, allowed to incubate for 30 minutes, diluted, and plated as described above. Vacuum-dried samples were rehydrated to approximately $1/5^{th}$ their original concentration, mixed to fully dissolve the pellet, diluted, and plated as described above. All samples were plated in at least triplicate. For these experiments, time zero is the time at which the samples were removed from the dryers. The preserved cell compositions that were prepared by freezing samples of the preservation medium in liquid nitrogen were plated as described above after complete thawing at room temperature had occurred.

The results for a given set of samples are set forth below in Table 1, where the numbers represent the percent of original activity that was recovered upon rehydration. The "solution" column provides the amount of viable cells in a given preservation medium, with the amount of viable cells in the "cells alone" sample being defined as 100%.

TABLE 1

| Sample | Solution | Frozen | Vacuum Dried | | | Freeze Dried | | | | |
|---|---|---|---|---|---|---|---|---|---|---|
| | | | Time = 0 | 9 days | 27 days | Time = 0 | 9 days | 28 days | 64 days | 101 days |
| Cells Alone | 100 | 105 | 0 | 0 | NA[3] | 56 | 0 | NA | NA | NA |
| 20% Trehalose + thio | 96 | 97 | 10 | 7 | NA | 44 | 31 | 21 | 5 | NA |
| 20% Trehalose + borate (0.3)[1] + thio[2] | 83 | 93 | 27 | 26 | 17 | 69 | 16 | 14 | 6 | NA |
| 20% Trehalose + NaH$_2$PO$_4$ (0.1) + thio | 89 | 88 | 12 | 6 | NA | 55 | 28 | 13 | 3 | NA |

TABLE 1-continued

| Sample | Solution | Frozen | Vacuum Dried | | | Freeze Dried | | | | |
|---|---|---|---|---|---|---|---|---|---|---|
| | | | Time = 0 | 9 days | 27 days | Time = 0 | 9 days | 28 days | 64 days | 101 days |
| 20% Trehalose + NaH$_2$PO$_4$ (0.3) + thio | 94 | 88 | 5 | 1 | NA | 45 | 24 | 7 | 0 | NA |
| 20% Trehalose + NaH$_2$PO$_4$ (0.5) + thio | 77 | 95 | 3 | 2 | NA | 51 | 26 | 0 | NA | NA |
| 20% Trehalose + NaH$_2$PO$_4$ (1.0) + thio | 92 | 86 | 3 | 2 | NA | 71 | 4 | NA | NA | NA |
| 20% Trehalose + thio + NaH$_2$PO$_4$/K$_2$HPO$_4$ (1.0) pH 5.6 | 103 | 105 | 51 | 48 | 39 | 84 | 72 | 58 | 17 | 0 |
| 20% Trehalose + thio + NaH$_2$PO$_4$/K$_2$HPO$_4$ (1.0), pH 4.9 | 106 | 107 | 4 | 3 | NA | 82 | 65 | 24 | 0 | NA |
| 20% Trehalose + thio + NaH$_2$PO$_4$/K$_2$HPO$_4$ (1.0), pH 6.6 | 93 | 106 | 52 | 59 | 73 | 82 | 76 | 70 | 67 | 57 |
| 20% Trehalose + thio + NaH$_2$PO$_4$/Na$_2$HPO$_4$ (1.0) pH 5.3 | 96 | 104 | 23 | 18 | 5 | 87 | 70 | 47 | 7 | NA |

[1]Numbers in parenthesis indicate the moles of phosphate ions per mole of trehalose.
[2]"thio" is shorthand for 1.9% sodium thiosulfate.
[3]NA: Samples with <10% recovery were not assayed at later time points.

EXAMPLE 2

The procedure of Example 1 was repeated, using phosphate, carbonate, or sulfate ions with polyhydroxy compounds in varying amounts. The results for a given set of samples are set forth below in Table 2, where the numbers represent the percent of original activity that was recovered upon rehydration. The "solution" column provides the amount of viable cells in a given preservation medium, with the amount of viable cells in the "cells alone" sample being defined as 100%.

TABLE 2

| Sample | Solution | Frozen | Vacuum Dried | | | Freeze Dried[4] | | | | |
|---|---|---|---|---|---|---|---|---|---|---|
| | | | Time = 0 | 19 days | 34 days | Time = 0 | 19 days | 38 days | 74 days | 99 days |
| Cells Alone | 100 | 102 | 2 | | | 46 | 0 | NA | NA | NA |
| 20% Trehalose + thio | 83 | 88 | 14 | 18 | NA[4] | 52 | 13 | 13 | 5 | NA |
| 20% Sucrose + thio | 100 | 103 | 4 | NA | NA | 80 | 33 | 19 | 20 | 15 |
| 20% Trehalose + borate(0.3)[1] + thio[2] | 101 | 90 | 37 | 21 | 21 | 49 | 0 | NA | NA | NA |
| 20% Sucrose + borate(0.3) + thio | 93 | 108 | 35 | 27 | NA | 55 | 3 | NA | NA | NA |
| 20% Trehalose[3] + Na$_2$CO$_3$ (1.0) + thio | 1 | 59 | 0 | NA | NA | 27 | 8 | NA | NA | NA |
| 20% Sucrose[3] + Na$_2$CO$_3$ (1.0) + thio | 1 | 34 | 0 | NA | NA | 16 | 0 | NA | NA | NA |
| 20% Trehalose + Na$_2$SO$_4$ (0.75) + thio | 87 | 92 | 24 | 21 | 18 | 73 | 1 | NA | NA | NA |
| 20% Sucrose + Na$_2$SO$_4$ (0.75) + thio | 91 | 86 | 8 | NA | NA | 66 | 7 | NA | NA | NA |

TABLE 2-continued

| Sample | Solution | Frozen | Vacuum Dried | | | Freeze Dried[4] | | | | |
|---|---|---|---|---|---|---|---|---|---|---|
| | | | Time = 0 | 19 days | 34 days | Time = 0 | 19 days | 38 days | 74 days | 99 days |
| 20% Trehalose + thio + NaH$_2$PO$_4$/ K$_2$HPO$_4$(1.0), pH 6.5 | 85 | 86 | 65 | 61 | 68 | 74 | 54 | 46 | 37 | 26 |
| 20% Sucrose + thio + NaH$_2$PO$_4$/ K$_2$HPO$_4$(1.0), pH 6.5 | 93 | 90 | 51 | 34 | NA | 74 | 43 | 29 | 27 | 12 |

[1]Numbers in parenthesis indicate the moles of phosphate, carbonate or sulfate ions per mole of polyhydroxy compound.
[2]"thio" is shorthand for 1.9% sodium thiosulfate.
[3]The pH was not controlled for these samples. Indicator paper estimated the pH at ~11. This is likely the source of the poor recovery.
[4]NA: Samples with <10% recovery were not assayed at later time points.

EXAMPLE 3

The procedure of Example 1 was repeated, using preservation media containing various sources of phosphate ions in varying amounts, and varying amounts of trehalose, with the exception that the freeze-dried samples were dried to 50° C. In addition, the residual water in the freeze-dried samples was measured by Karl Fischer (KF) analysis, and the glass transition temperature ($T_g$) was obtained. The results for a given set of samples are set forth below in Table 3, where the numbers represent the percent of original activity that was recovered upon rehydration. The "solution" column provides the amount of viable cells in a given preservation medium, with the amount of viable cells in the "cells alone" sample being defined as 100%.

TABLE 3

| Sample | % water by KF | $T_g$ (° C.) | Solution | Frozen | Vacuum Dried | | | Freeze Dried | | | |
|---|---|---|---|---|---|---|---|---|---|---|---|
| | | | | | Time = 3 | 19 days | 95 days | Time = 0 | 21 days | 48 days | 92 days |
| Cells Alone | 0.8 | 47 | 100 | 10 | 0 | NA | NA | 22 | 0 | NA | NA |
| 20% Trehalose + thio | 0.7 | 88 | 105 | 104 | 9 | NA | NA | 50 | 10 | NA | NA |
| 20% Trehalose + thio[2] + NaH$_2$PO$_4$/ K$_2$HPO$_4$(0.5)[1], ph 6.6 | 5.3 | 32 | * | 105 | 68 | 78 | 50 | 44 | 27 | 15 | 5 |
| 20% Trehalose + thio + NaH$_2$PO$_4$/ K$_2$HPO$_4$(1), pH 6.6 | 3.2 | 85 | 105 | 114 | 75 | 89 | 70 | 66 | 63 | 55 | 48 |
| 20% Trehalose + thio + NaH$_2$PO$_4$/ K$_2$HPO$_4$(1), pH 6.6 + Methanol | 1.6 | 46 | 87 | 87 | 51 | 59 | 5 | 69 | 41 | 27 | 13 |
| 20% Trehalose + thio + KH$_2$PO$_4$/ K$_2$HPO$_4$(1), pH 6.6 | 3.5 | 82 | 97 | 110 | 70 | 63 | 54 | 70 | 60 | 61 | 49 |
| 5% Trehalose + thio + NaH$_2$PO$_4$/ K$_2$HPO$_4$(1), pH 6.6 | 3.8 | 44 | 108 | 110 | 35 | 19 | 27 | 51 | 26 | 9 | NA |

Note:
[1]Numbers in parenthesis indicate the moles of phosphate ions per mole of trehalose.
[2]"thio" is shorthand for 1.9% sodium thiosulfate.
*This sample was improperly diluted, resulting in a recovery >400%.

EXAMPLE 4

The procedure of Example 1 was repeated, using varying amounts of trehalose and different phosphate ion sources in the preservation medium, with the exception that the freeze-dried samples were dried to a temperature of 50° C. In two samples, ethanol was added as a drying agent to the preservation medium, while in one sample, the *L. acidophilus* cells were "washed" (centrifuged, decanted and resuspended) to remove residual growth medium. Media containing different buffers were also tested. The results for a given set of samples are set forth below in Table 4, where the numbers represent the percent of original activity that was recovered upon rehydration. The "solution" column provides the amount of viable cells in a given preservation medium, with the amount of viable cells in the "cells alone" sample being defined as 100%.

TABLE 4

| | | | Vacuum Dried | | Freeze Dried[3] | | | |
|---|---|---|---|---|---|---|---|---|
| Sample | Solution | Frozen | 40 days | 68 days | Time = 0 | 14 days | 40 days | 68 days |
| Cells Alone | 100 | 116 | 0 | NA | 36 | 0 | NA | |
| 20% Trehalose + thio[2] | 89 | 98 | 22 | 8 | 73 | 28 | 4 | |
| 17.5% Trehalose + thio + $KH_2PO_4/K_2HPO_4(1)$[1], pH 6.5 | 101 | 120 | 41 | 55 | 65 | 85 | 23 | 22 | 7 |
| 17.5% Trehalose + thio + $KH_2PO_4/K_2HPO_4(1)$, pH 6.5 + Ethanol (1 mol/mol P) | 98 | 112 | 0 | NA | 48 | 9 | NA | |
| 17.5% Trehalose + thio + $KH_2PO_4/K_2HPO_4(1)$, pH 6.5 + Ethanol (2 mol/mol P) | 89 | 95 | 0 | NA | 14 | 0 | NA | |
| 20% Trehalose + thio + $K_2HPO_4(1)$ | 106 | 97 | 55 | 44 | 30 | 77 | 50 | 63 | 54 |
| 20% Trehalose + thio + $K_2HPO_4(1)$ + citric acid/NH3OH buffering | 59 | 49 | 4 | NA | 47 | 15 | 27 | 29 |
| 20% Trehalose + thio + $K_2HPO_4(1)$ + lactic acid/NH3OH buffering | 59 | 48 | 3 | NA | 27 | 6 | NA | |
| 17.5% Trehalose + thio + $KH_2PO_4/K_2HPO_4(1)$, pH 6.5 Washed Cells | 97 | 122 | 40 | 41 | 24 | 80 | 30 | 20 | 6 |

[1]Numbers in parenthesis indicate the moles of phosphate ions per mole of trehalose.
[2]"thio" is shorthand for 1.9% sodium thiosulfate.
[3]NA: Samples with <10% recovery were not assayed at later time points.

EXAMPLE 5

The procedure of Example 1 was repeated, using trehalose, phosphate ions, and various antioxidants or no antioxidant, with the exception that the samples were freeze-dried to a temperature of 50° C. The results for a given set of samples are set forth below in Table 5, where the numbers represent percent of original activity that was recovered upon rehydration. The "solution" column provides the amount of viable cells in a given preservation medium, with the amount of viable cells in the "cells alone" sample being defined as 100%.

TABLE 5

| | | | Vacuum Dried | | | Freeze Dried | | |
|---|---|---|---|---|---|---|---|---|
| Sample | Solution | Frozen | Time = 0 | 9 days | 25 days | Time = 0 | 9 days | 25 days |
| Cells Alone | 100 | 100 | 0 | 0 | 0 | 1 | 0 | 0 |
| 20% Trehalose + $KH_2PO_4/K_2HPO_4(1)$[1, 3] | 99 | 85 | 25 | 30 | 15 | 65 | 51 | 33 |
| 20% Trehalose + $KH_2PO_4/K_2HPO_4(1)$[1, 3] + thio[2] | 80 | 71 | 46 | 35 | 20 | 73 | 42 | 19 |
| 20% Trehalose + $KH_2PO_4/K_2HPO_4(1)$[1, 3] + ascorbic acid | 95 | 82 | 33 | 30 | 16 | 61 | 38 | 25 |

TABLE 5-continued

| Sample | Solution | Frozen | Vacuum Dried | | | Freeze Dried | | |
|---|---|---|---|---|---|---|---|---|
| | | | Time = 0 | 9 days | 25 days | Time = 0 | 9 days | 25 days |
| 20% Trehalose + $KH_2PO_4/K_2HPO_4(1)^{1,\,3}$ + citric acid | 80 | 75 | 16 | 24 | 11 | 49 | 17 | 3 |
| 20% Trehalose + $KH_2PO_4/K_2HPO_4(1)^{1,\,3}$ + sodium citrate | 88 | 76 | 42 | 24 | 10 | 74 | 46 | 12 |

Note:
[1]Numbers in parenthesis indicate the moles of phosphate ions per mole of trehalose.
[2]"thio" is shorthand for sodium thiosulfate.
[3]The pH of the trehalose-phosphate was targeted at 6.5 but was not measured after addition of antioxidant or cells. The final pH was most likely between 6.0 and 6.5.

EXAMPLE 6

The procedure of Example 1 was repeated, with the exceptions that a *Pediococcus* species was substituted for *L. acidophilus* cells, and the freeze-dried samples were dried to a temperature of 25° C. or further dried to 50° C. The results for a given set of samples are set forth below in Table 6, where the numbers represent percent of original activity that was recovered upon rehydration. The "solution" column provides the amount of viable cells in a given preservation medium, with the amount of viable cells in the "cells alone+thio" sample being defined as 100%.

reaction mixture contained 100 mM potassium phosphate buffer (pH 7.5), 0.150 mM NADH, and 1.20 mM pyruvic acid.

To prepare the samples, the dialyzed LDH was diluted with the same potassium phosphate buffer that had been used for dialysis. The resulting enzyme solution had a phosphate ion concentration of 100 mM, and a LDH concentration of 50 µg/ml. Three sets of protectant mixtures were then made. The mixture sets had a trehalose concentration of 200 mM, 400 mM and 600 mM, respectively. Each mixture set consisted of four separate protectant samples, containing

TABLE 6

| Sample | Solution | Frozen | Vacuum Dried | | | Freeze Dried $T_{final}$ = 25 C. | Freeze Dried $T_{final}$ = 50 C. | Freeze Dried $T_{final}$ = 25 C. | | Freeze Dried $T_{final}$ = 50 C. | |
|---|---|---|---|---|---|---|---|---|---|---|---|
| | | | Time = 0 | 31 days | 60 days | Time = 0 | Time = 0 | 31 days | 60 days | 31 days | 59 days |
| Cells Alone + thio | 100 | 118 | 73 | 62 | 75 | 96 | 73 | 5 | | 2 | |
| 20% Trehalose + thio[2] | 121 | 121 | 84 | 61 | 32 | 117 | 115 | 55 | 19 | 48 | 25 |
| 20% Trehalose + thio + $KH_2PO_4/K_2HPO_4(1)^{1,\,3}$ | 114 | 113 | 104 | 95 | 89 | 100 | 113 | 96 | 78 | 97 | 97 |
| 20% Trehalose + $KH_2PO_4/K_2PO_4(1)^{1,\,3}$ + 2% Citric Acid | 102 | 122 | 99 | 93 | 81 | 118 | 94 | 75 | 65 | 88 | 81 |

Note:
[1]Numbers in parenthesis indicate the moles of phosphate ions per mole of trehalose.
[2]"thio" is shorthand for 1.9% sodium thiosulfate.
[3]The pH of the trehalose-phosphate was measured at 6.5 prior to mixing with cells. The final pH was most likely below 6.5.

EXAMPLE 7

$_L$-Lactate dehydrogenase (LDH, EC 1.1.1.27, Type II, rabbit muscle) was dialyzed overnight at 4° C. in 100 mM potassium phosphate buffer solution at pH 7.5. The total protein content was assayed using SIGMA DIAGNOSTIC, a protein determination kit purchased from Sigma Chemical Company (St. Louis, Mo.), using the modified biuret method of Ohnishi and Barr, "Simplified Method for Quantitating Protein using the Biuret and Phenol Reagents," *Analytical Biochem.* 86:193–200 (1978). The protein assay was conducted at the characteristic absorption at 725 nm at room temperature using a Varian UV Spectrophotometer. The phosphate ions in a concentration of 100 mM, 300 mM, 500 mM and 700 mM, respectively. These samples were made by dissolving the trehalose in an aqueous phosphate solution containing a given amount of phosphate ions.

Two milliliters of the LDH solution were then mixed with 2 ml of each of the twelve protectant mixtures to provide 4 ml solutions of aqueous preservation media having a trehalose concentration of either 100 mM, 200 mM, or 300 MM, LDH concentration of 25 µg/ml, and phosphate ion concentrations of 100 mM, 200 mM, 300 mM or 400 mM. The above sample preparation is shown in Table 7.

TABLE 7

| Sample | 1 | 2 | 3 | 4 |
|---|---|---|---|---|
| (Set 1) | | | | |
| Enzyme Solution | 50 µg/ml LDH<br>100 mM Phosphate | 50 µg/ml LDH<br>100 mM Phosphate | 50 µg/ml LDH<br>100 mM Phosphate | 50 µg/ml LDH<br>100 mM Phosphate |
| Cryoprotective Solution | 200 mM Trehalose<br>100 mM Phosphate | 200 mM Trehalose<br>100 + 200 mM Phosphate | 200 mM Trehalose<br>100 + 400 mM Phosphate | 200 mM Trehalose<br>100 + 600 mM Phosphate |
| Mixture Solution | 25 µg/ml LDH<br>100 mM Trehalose<br>100 mM Phosphate | 25 µg/ml LDH<br>100 mM Trehalose<br>200 mM Phosphate | 25 µg/ml LDH<br>100 mM Trehalose<br>300 mM Phosphate | 25 µg/ml LDH<br>100 mM Trehalose<br>400 mM Phosphate |
| (Set 2) | | | | |
| Enzyme Solution | 50 µg/ml LDH<br>100 mM Phosphate | 50 µg/ml LDH<br>100 mM Phosphate | 50 µg/ml LDH<br>100 mM Phosphate | 50 µg/ml LDH<br>100 mM Phosphate |
| Cryoprotective Solution | 400 mM Trehalose<br>100 mM Phosphate | 400 mM Trehalose<br>100 + 200 mM Phosphate | 400 mM Trehalose<br>100 + 400 mM Phosphate | 400 mM Trehalose<br>100 + 600 mM Phosphate |
| Mixture Solution | 25 µg/ml LDH<br>200 mM Trehalose<br>100 mM Phosphate | 25 µg/ml LDH<br>200 mM Trehalose<br>200 mM Phosphate | 25 µg/ml LDH<br>200 mM Trehalose<br>300 mM Phosphate | 25 µg/ml LDH<br>200 mM Trehalose<br>400 mM Phosphate |
| (Set 3) | | | | |
| Enzyme Solution | 50 µg/ml LDH<br>100 mM Phosphate | 50 µg/ml LDH<br>100 mM Phosphate | 50 µg/ml LDH<br>100 mM Phosphate | 50 µg/ml LDH<br>100 mM Phosphate |
| Cryoprotective Solution | 600 mM Trehalose<br>100 mM Phosphate | 600 mM Trehalose<br>100 + 200 mM Phosphate | 600 mM Trehalose<br>100 + 400 mM Phosphate | 600 mM Trehalose<br>100 + 600 mM Phosphate |
| Mixture Solution | 25 µg/ml LDH<br>300 mM Trehalose<br>100 mM Phosphate | 25 µg/ml LDH<br>300 mM Trehalose<br>200 mM Phosphate | 25 µg/ml LDH<br>300 mM Trehalose<br>300 mM Phosphate | 25 µg/ml LDH<br>300 mM Trehalose<br>400 mM Phosphate |

Forty-eight vials were then prepared for each of the above samples of preservation media. Each vial was labeled and weighed, and 1 ml of preservation medium was pipetted into each vial. Each vial was then reweighed. The samples were then frozen by immersion of the vials in liquid nitrogen ("quench") or by placement in the freeze-dryer on precooled shelves at a temperature no greater than −45° C. ("slow freeze"). All of the freeze-dried samples were subjected to the following freeze-drying protocol in a Virtis 12EL freeze-dryer, where all pressures and temperatures are set points. After the samples were placed in the freeze-dryer as discussed above, the freeze-dryer was evacuated with a pressure of 0 mtorr. The samples were held at −45° C. and 0 mtorr for 600 minutes, after which the temperature and pressure were increased to −40° C. and 20 mtorr, respectively, over a period of 50 minutes. The samples where then held at −40° C. and 20 mtorr for 600 minutes. The temperature was then increased to −35° C. over a period of 50 minutes, and the samples were then held at −35° C. and 20 mtorr for 600 minutes. The temperature and pressure were next increased to −30° C. and 50 mtorr, respectively, over 50 minutes and the samples were then held at −30° C. and 50 mtorr for 600 minutes. At the end of that period of time, the temperature and pressure were increased to −25° C. and 100 mtorr, respectively, over 50 minutes, and the samples were held at −25° C. and 100 mtorr for 600 minutes. The temperature was then increased to −20° C. over 50 minutes, and the samples were then held at −20° C. and 100 mtorr for 600 minutes. The temperature was next increased to −10° C. over 100 minutes, and the samples were held at that temperature and 100 mtorr for 600 minutes.

The samples were then increased to a temperature of 25° C. at 50 mtorr over a period of 700 minutes. The samples were then held at the final temperature at 0 mtorr for 2140 minutes until unloading. The freeze dryer was then vented with nitrogen gas, and the preserved LDH samples in the vials were removed and measured for LDH activity. Before the activity was measured, each sample was weighed to determine the amount of water loss, and rehydrated with purified water (Millipore System from Millipore Corp.) in the amount of the water that was lost. LDH activity was then determined using the same method discussed previously.

Figure 1:
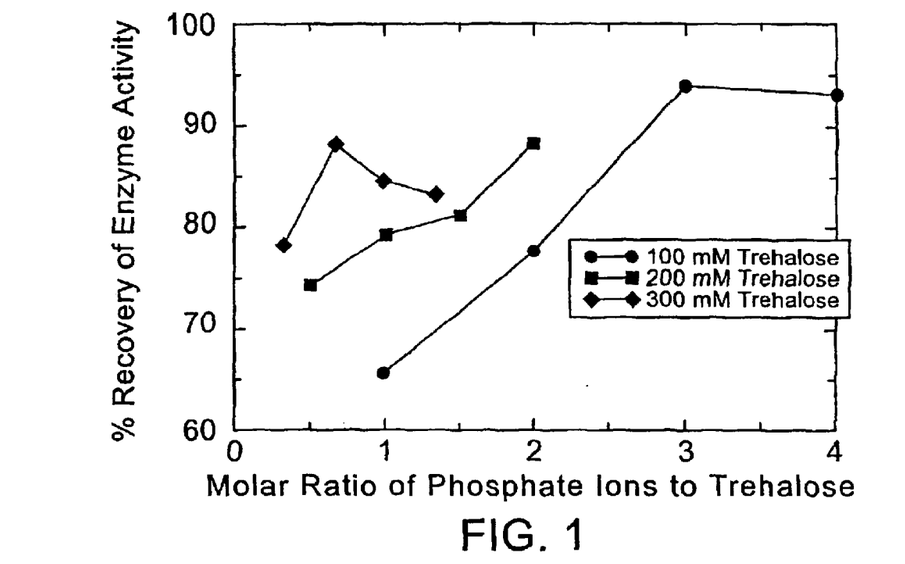
FIG. 1 is a graph of percent activity recovered from freeze-dried lactate dehydrogenase compositions made using varying amounts and molar ratios of phosphate and trehalose.
Figure 2:
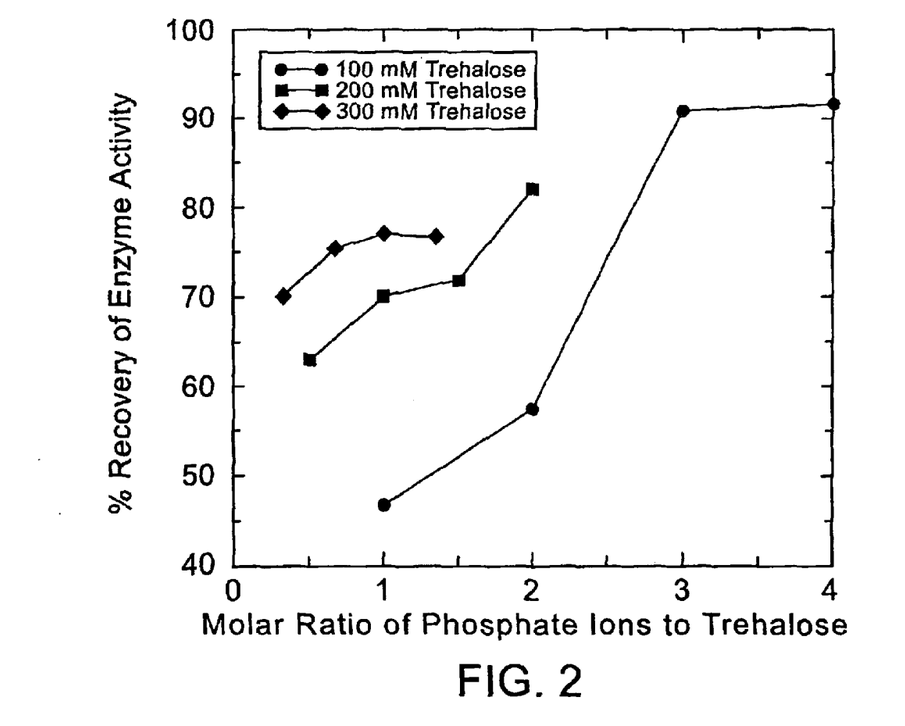
FIG. 2 is a graph of percent activity recovered from frozen lactate dehydrogenase compositions made using varying amounts and molar ratios of phosphate and trehalose.

The results for a given set of samples are set forth in FIG. 1 (freeze-drying) and FIG. 2 (freezing).

EXAMPLE 8

$_L$-Lactate dehydrogenase (LDH, EC 1.1.1.27, Type II, rabbit muscle) was dialyzed overnight at 4° C. in 100 mM potassium phosphate buffer solution at pH 7.5. The total protein content was assayed using SIGMA DIAGNOSTIC, a protein determination kit purchased from Sigma Chemical Company (St. Louis, Mo.), using the modified biuret method of Ohnishi and Barr, "Simplified Method for Quantitating Protein using the Biuret and Phenol Reagents," *Analytical Biochem.* 86:193–200 (1978). The protein assay was conducted at the characteristic absorption at 725 nm at room temperature using a Varian UV Spectrophotometer. The reaction mixture contained 100 mM potassium phosphate buffer (pH 7.5), 0.150 mM NADH, and 1.20 mM pyruvic acid.

To prepare the samples, LDH was added to four 50 ml containers and diluted with the same potassium phosphate buffer that had been used for dialysis to make a 25 ml solution. In each of the samples, the enzyme concentration was 50 µg/ml. Four protectant mixtures having a volume of 25 ml were then prepared in 50 ml containers. Each mixture contained 400 mM of trehalose, and varying amounts of phosphate ion. To make the first mixture (reference), the trehalose was dissolved in 10 mM potassium phosphate solution. For the second mixture, the trehalose was dissolved in 100 mM potassium phosphate solution. The third and fourth mixtures were made by dissolving the trehalose in 500 mM potassium phosphate solution and 900 mM potassium phosphate solution, respectively.

The LDH samples were then mixed with the protectant mixtures to provide 50 ml solutions of aqueous preservation media having a LDH concentration of 25 µg/ml, a trehalose concentration of 200 mM and varying LDH and phosphate ion concentrations. The phosphate ion concentration for samples 1–4 was 10 mM, 100 mM, 300 mM, and 500 mM, respectively, for a phosphate ion to trehalose molar ratio of 0.05 for Sample 1, 0.5 for Sample 2, 1.5 for Sample 3, and 2.5 for Sample 4. The above sample preparation is shown below in Table 8.

TABLE 8

| Sample | 1 | 2 | 3 | 4 |
| --- | --- | --- | --- | --- |
| LDH Solution | 50 μg/ml LDH<br>10 mM phosphate | 50 μg/ml LDH<br>100 mM phosphate | 50 μg/ml LDH<br>100 mM phosphate | 50 μg/ml LDH<br>100 mM phosphate |
| Protectant Mixture | 400 mM trehalose<br>10 mM phosphate | 400 mM trehalose<br>100 mM phosphate | 400 mM trehalose<br>500 mM phosphate | 400 mM trehalose<br>900 mM phosphate |
| Preservation Medium | 25 μg/ml LDH<br>200 mM trehalose<br>10 mM phosphate | 25 μg/ml LDH<br>200 mM trehalose<br>100 mM phosphate | 25 μg/ml LDH<br>200 mM trehalose<br>300 mM phosphate | 25 μg/ml LDH<br>200 mM trehalose<br>500 mM phosphate |

Forty vials were then prepared for each of the above four samples of preservation media. Each vial was labeled and weighed, and 1 ml of preservation medium was pipetted into each vial. Each vial was then reweighed. The samples were then freeze-dried using the same protocol as described in Example 7.

After freeze-drying was complete, the preserved LDH samples in the vials were removed, the vials were sealed, and stored in either a 37° C. incubator, a 30° C. incubator or at 4° C. in a refrigerator.

LDH activity was then measured periodically for the samples. Before the activity was measured, each sample was weighed to determine the amount of water loss, and rehydrated with purified water (MilliQ System from Millipore Corp.) in the amount of the water that was lost. LDH activity was then determined using the same method discussed previously.

Figure 3:
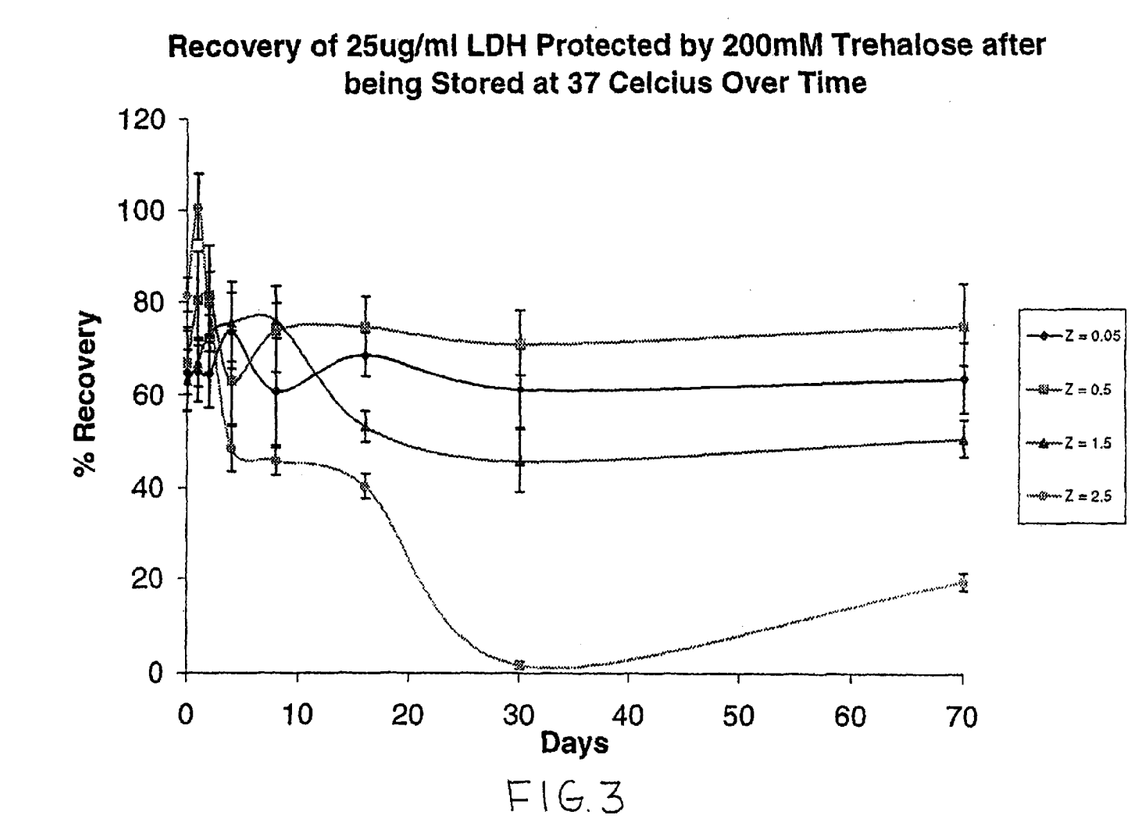
FIG. 3 is a graph of percent activity recovered over time from freeze-dried lactate dehydrogenase compositions made using varying amounts and molar ratios of phosphate and trehalose.
Figure 4:
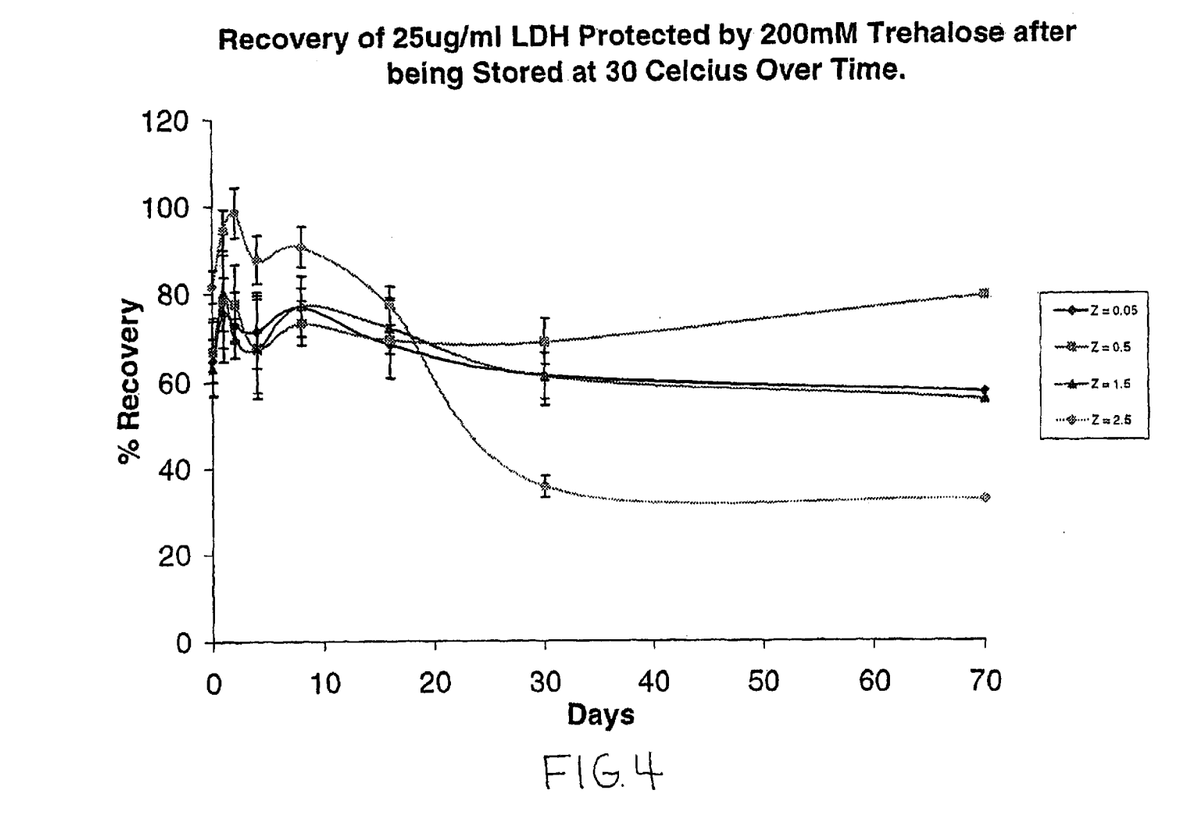
FIG. 4 is a graph of percent activity recovered over time from freeze-dried lactate dehydrogenase compositions made using varying amounts and molar ratios of phosphate and trehalose.
Figure 5:
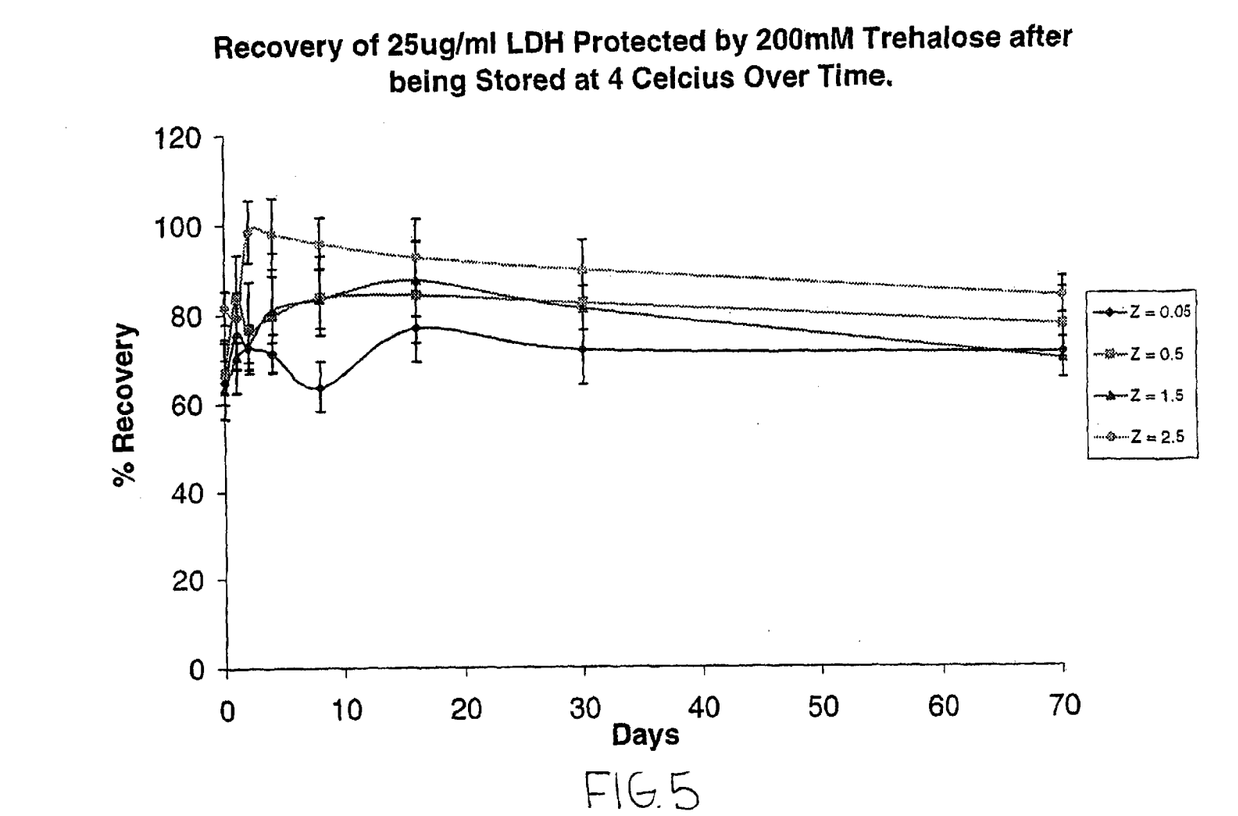
FIG. 5 is a graph of percent activity recovered over time from freeze-dried lactate dehydrogenase compositions made using varying amounts and molar ratios of phosphate and trehalose.

The results for a given set of samples are set forth in FIGS. 3–5, where "Z" is the molar ratio of phosphate ions to trehalose.

EXAMPLE 9

The procedure of Example 1 was repeated. The results are set forth below in Table 9, where the numbers represent percent of original activity that was recovered upon rehydration. The "solution" column provides the amount of viable cells in a given preservation medium, with the amount of viable cells in the "cells alone" sample being defined as 100%.

TABLE 9

| Sample | Solution | Frozen | Freeze Dried T = 3 days |
| --- | --- | --- | --- |
| Cells Alone | 100 | 105 | 0 |
| 20% Trehalose | 91 | 89 | 11 |
| 20% Trehalose + thio[2] | 89 | 77 | 8 |
| 20% Trehalose + KH$_2$PO$_4$/K$_2$HPO$_4$(1)[1], pH 6.4 | 72 | 78 | 39 |
| 20% Trehalose + thio + KH$_2$PO$_4$/K$_2$HPO$_4$(1), pH 6.4 | 54 | 61 | 41 |
| Cells + KHPO$_4$/K$_2$HPO$_4$ (Same phosphate per g cells as Samples 4, 5 above) | 89 | 90 | 7 |
| 20% Trehalose + thio + K$_2$HPO$_4$(1) | 75 | 81 | 39 |

Note:
[1]Numbers in parenthesis indicate the moles of phosphate ions per mole of trehalose.
[2]"thio" is shorthand for 1.9% sodium thiosulfate.

EXAMPLE 10

Figure 6:
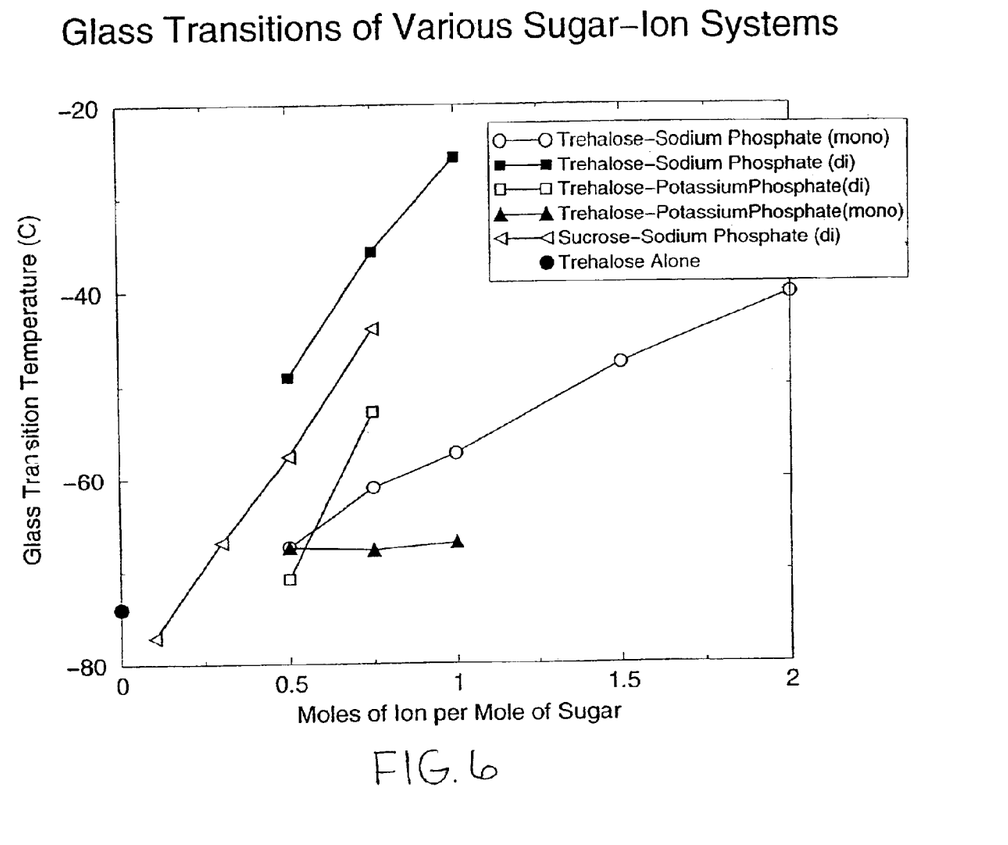
FIG. 6 is a graph of glass transition temperatures for various protectant mixtures of the invention.

Aqueous protectant mixtures containing 7.5% of sucrose or trehalose on a molar basis and varying amounts of phosphate ions provided by either potassium monophosphate or potassium diphosphate were prepared, and 25 microliters of each mixture was sealed into an aluminum Differential Scanning Calorimetry pan. The samples were then quenched by immersion in liquid nitrogen and loaded into the Differential Scanning Calorimeter, which had been precooled to −140° C. The samples were then scanned at a rate of 5° C./min to a temperature of 50° C., and the glass transition temperature ($T_g$) was determined. The results for each sample are shown in FIG. 6.

We claim:

1. A method of preparing a preserved biological material composition comprising:
   (a) forming an aqueous preservation medium comprising (i) a biological material; (ii) at least one polyhydroxy compound, where the total amount of polyhydroxy compound in the medium is from 10% to about 60% by weight of the medium; and (iii) phosphate ions, where the total amount of phosphate ions in the medium is such that the molar ratio of phosphate ions to moles of hydroxyl groups in the polyhydroxy compound is from about 0.025 to about 0.625; and
   (b) preserving the aqueous preservation medium using at least one preservation process.

2. The method of claim 1, where the preservation processes are one or more processes selected from the group consisting of freezing, freeze-drying, ambient-air drying, vacuum-drying, and spray-drying.

3. The method of claim 1, where the pH of the medium is about 5 to about 10.

4. The method of claim 1, where the polyhydroxy compound is selected from a group consisting of monosaccharides, disaccharides, and polysaccharides.

5. The method of claim 1, where the polyhydroxy compound is trehalose.

6. The method of claim 1, where the total amount of polyhydroxy compound in the medium is from 10% to about 30% by weight of the medium.

7. The method of claim 4, where the total amount of polyhydroxy compound in the medium is from 10% to about 30% by weight of the medium.

8. The method of claim 1, where the molar ratio of phosphate ions to moles of hydroxyl groups in the polyhydroxy compound is from about 0.0375 to about 0.625.

9. The method of claim 1, where the biological material is selected form the group consisting of cells, proteins, and enzymes.

10. A method of preparing a preserved biological material composition comprising:
    (a) forming an aqueous preservation medium comprising (i) a biological material; (ii) trehalose, where the total amount trehalose in the medium is from 10% to about 60% by weight of the medium; and (iii) phosphate ions, where the total amount of phosphate ions in the medium is such that the molar ratio of phosphate ions to trehalose is from about 0.2 to about 5; and (b) preserving the aqueous preservation medium using at least one preservation process.

11. The method of claim 10, where the preservation processes are one or more processes selected from the group consisting of freezing, freeze-drying, ambient-air drying, vacuum-drying, and spray-drying.

12. The method of claim 10, where the trehalose is present in an amount from 10% to about 30% by weight of the medium.

13. The method of claims 12, where the pH is from about 5 to about 10.

14. The method of claim 13, where the molar ratio of phosphate ions to trehalose is from about 0.3 to about 5.

15. The method of claim 10, where the biological material is selected from the group consisting of cells, proteins, and enzymes.

* * * * *